United States Patent

Hay et al.

[11] Patent Number: 5,306,789
[45] Date of Patent: Apr. 26, 1994

[54] AMORPHOUS, SOLUBLE, AROMATIC POLYMERS WITH HIGH GLASS TRANSITION TEMPERATURES

[76] Inventors: Allan S. Hay, 5015 Glencairn Avenue, Montreal, Quebec H3W 1B3; Rina Singh, 1190 Fort Street, Apt. #704, Montreal, Quebec H3H 2B5, both of Canada

[21] Appl. No.: 606,160

[22] Filed: Oct. 31, 1990

[51] Int. Cl.$^5$ .................. C08G 10/00; C08G 61/10; C08G 61/12; C08G 65/00
[52] U.S. Cl. .................. 525/471; 528/125; 528/126; 528/171; 528/174; 528/226; 528/229; 528/176; 528/179; 528/225
[58] Field of Search ............... 528/176, 179, 219, 225, 528/125, 126, 171, 174, 175, 219, 226, 229, 394, 397; 525/471

[56] References Cited

U.S. PATENT DOCUMENTS

| | | | |
|---|---|---|---|
| 3,441,538 | 4/1969 | Marks | 528/173 |
| 3,442,857 | 5/1969 | Thornton | 528/179 |
| 4,176,222 | 11/1979 | Cinderey et al. | 528/174 |
| 4,954,604 | 9/1990 | Genz et al. | 528/125 |
| 5,053,477 | 10/1991 | Kern et al. | 528/125 |

OTHER PUBLICATIONS

Iijima et al. "Modification of Epoxy Resins with Poly(Aryl Ether Ketone)s" Journal of Applied Polymer Science, vol. 43, 1685-1692 (1991).

*Primary Examiner*—John Kight, III
*Assistant Examiner*—Jeffrey Culpeper Mullis
*Attorney, Agent, or Firm*—Bachman & LaPointe

[57] ABSTRACT

Amorphous polymers which are soluble in organic solvents and can thus be cast as films have high glass transition temperatures which make them suitable for numerous high temperature applications; the polymers comprise ortho aromatic polyketones, polyphthalazines and polyisoquinolines, the polyphthalazines and polyisoquinolines being readily formed from the polyketones.

10 Claims, No Drawings

AMORPHOUS, SOLUBLE, AROMATIC POLYMERS WITH HIGH GLASS TRANSITION TEMPERATURES

BACKGROUND OF THE INVENTION a) Field of the Invention

This invention relates to aromatic polymers which are amorphous and readily soluble in organic solvents, can be formed with a wide range of glass transition temperatures and can be cast to provide tough, transparent, flexible films; copolymers can also be synthesized; the invention also relates to processes for producing the polymers. The invention is more especially concerned with polyketones, polyphthalazines and polyisoquinolines.

b) Description of Prior Art

Polyetherketones that are para-substituted are commercial materials with modest glass transition temperatures and relatively high melting points; polyetherketones with meta substitution have also been synthesized (P. M. Hergenrother et al, J. Polymer Prepr.—[Am. Chem. Soc., Div. Polym. Chem.] 1985, Vol. 26, page 174).

Polyquinolines have been synthesized (J. K. Stille et al, Polym. Chem. Ed., 1975, Vol. 13, page 2233; Macromolecules, 1976, Vol. 9, pages 489 and 496) and exhibit high stiffness and high glass transition temperatures. These polyquinolines are relatively insoluble. One approach to improving the solubility without loss of thermal stability has been the introduction of flexible groups into the polymer backbone, and depending on the chemical repeat unit structure, high molecular weight polyquinolines exhibit a Tg ranging from 250° to 400° C. These polyquinolines are produced by a complex synthesis from costly starting materials and have not been exploited.

SUMMARY OF THE INVENTION

It is an object of this invention to provide new aromatic polymers.

It is a further object of this invention to provide such polymers which are amorphous and soluble and exhibit a high Tg.

It is still a further object of this invention to provide processes for preparing the new polymers.

It is yet another object of the invention to provide epoxidized polymers and processes for their preparation.

In accordance with the invention novel polymers have formula (I):

$$\text{(I)}\quad \begin{array}{c} A_2 \quad A_3 \\ A_1 - \!\!\!\bigcirc\!\!\!- A_4 \\ (\!\!\text{-}Ar_1\!\!-\!\!B \quad D\!\!-\!\!Ar_2\!\!-\!\!X\!\!\text{-})_n \end{array}$$

wherein $A_1$, $A_2$, $A_3$ and $A_4$ are each independently selected from hydrogen, aryl and hetaryl, said aryl and hetaryl being unsubstituted or substituted one or more times by a substituent selected from lower alkyl, lower alkoxy, lower thialkyl, halogen, aryl and hetaryl, B and D are both carbonyl groups CO, or B and D together represent a divalent radical of formula:

$$-C=N-N=C- \quad \text{or} \quad -C=N-\!\!\overset{Ar_3}{\underset{|}{C}}\!\!=C$$
$$\text{(II)} \qquad\qquad\qquad \text{(III)}$$

wherein $Ar_3$ is aryl or hetaryl, unsubstituted or substituted one or more times by a substituent selected from lower alkyl, lower alkoxy, lower thioalkyl, halogen, aryl and hetaryl, $Ar_1$ and $Ar_2$ are each phenylene radicals, unsubstituted or substituted 1 to 4 times by a substituent selected from lower alkyl, lower alkoxy, lower thioalkyl, halogen, aryl and hetaryl, n is an integer of 20 to 200, preferably 30 to 150, X is a single bond, —O—R—O—, —S— or —S—R—S—, in which R is arylene or aralkarylene, in which each arylene moiety is unsubstituted or substituted by lower alkyl, lower thioalkyl, halogen, aryl or hetaryl, and the alk. moiety is unsubstituted or substituted by halogen.

When B and D are carbonyl the polymers (I) are polyketones; when B and D together represent a divalent racical (II) a pyridazine ring is formed and the polymers (I) are polyphthalazines; and when B and D together represent a divalent radical (III), a pyridine ring is formed and the polymers (I) are polyisoquinolines.

In another aspect of the invention processes are provided for producing the polymers (I).

DESCRIPTION OF PREFERRED EMBODIMENTS

The aryl radicals in the polymers (I) are in particular phenyl, naphthyl or anthracyl; the hetaryl radicals in the polymers (I) are in particular heteroaromatic radicals containing one or more heteroatoms selected from nitrogen, oxygen and sulphur in the aromatic ring.

Typical nitrogen-containing heteroaromatics include pyridine, pyrazine and quinoline; typical sulphur-containing aromatics include thiophene and benzothiophene; typical oxygen-containing aromatics include furan, dibenzofuran and diphenyl ether.

The lower alkyl, alkoxy and thioalkyl substituents suitably have 1 to 6, preferably 1 to 4 carbons.

The halogen atoms are in particular fluorine, chlorine, bromine or iodine atoms.

The arylene radicals R are in particular phenylene, naphthylene and anthracylene radicals.

The arylene moieties in the aralkarylene radicals R are in particular phenylene, naphthylene and anthracylene moieties, unsubstituted or substituted as described above; and the alk. moiety is in particular alkylidene of 1 to 6 carbon atoms, unsubstituted or fluoro-substituted, for example, hexafluoro-isopropylidene.

The aralkarylene radicals R are in particular a radical:

—Ph—R$_1$—Ph— in which $R_1$ is a straight chain or branched alkylene of 1 to 6 carbon atoms, and Ph is phenylene.

Process of Preparation of Polymers (I)

The synthesis of the polymers I is described and illustrated for the embodiment in which $A_1$, $A_2$, $A_3$ and $A_4$ are all hydrogen atoms.

In accordance with a first process illustrated in Scheme I:

Di-(p-fluorobenzoyl)ethylene (1) is reacted with 1,3-butadiene under conditions for the Diels-Alder reaction, particularly in refluxing benzene to produce the substituted cyclohexene (2).

This reaction proceeds in quantitative yield; the reaction mixture changes from a bright yellow to a colourless solution indicative of completion of the reaction;

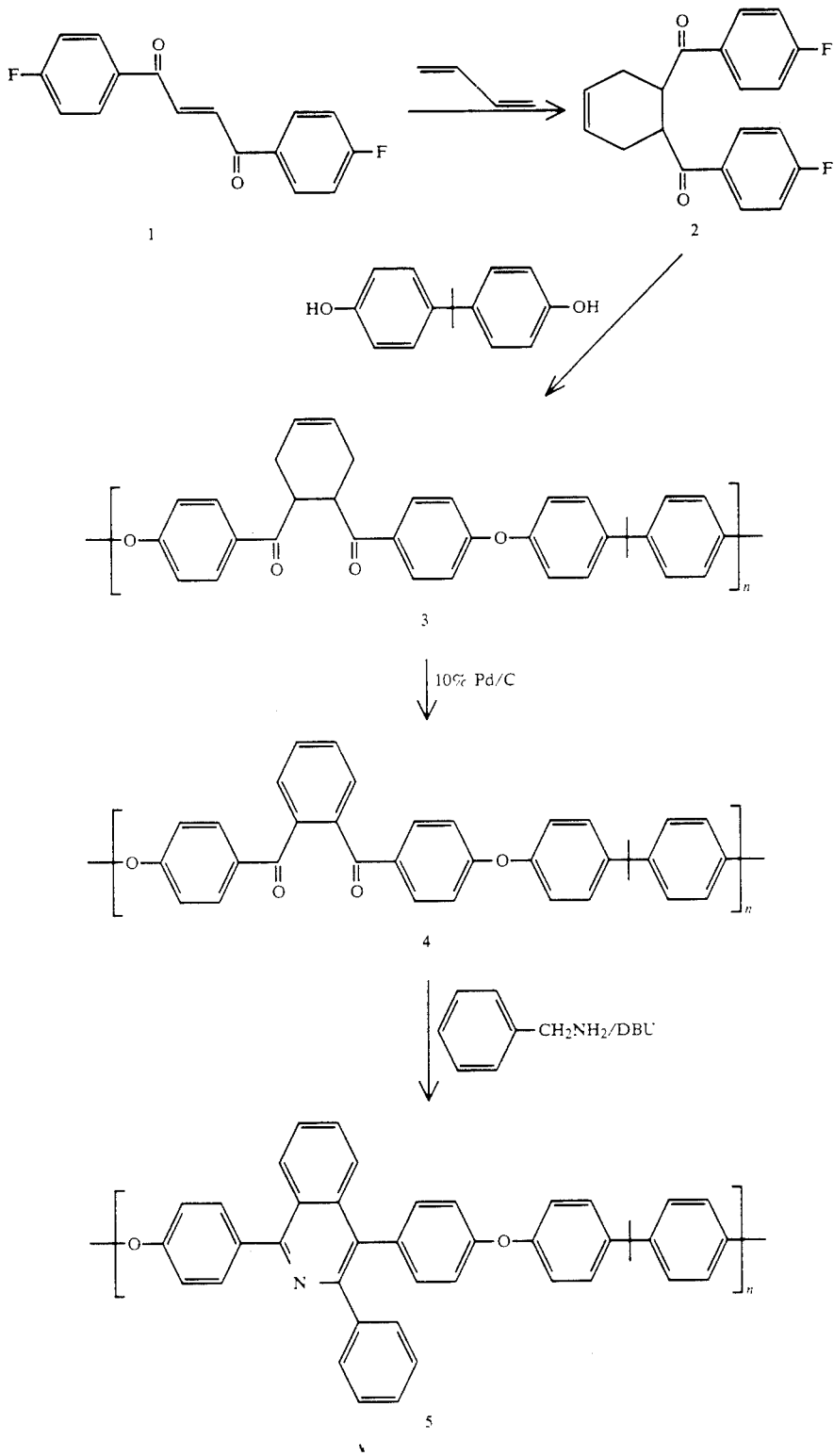

Scheme I the substituted cyclohexene (2) is obtained in high purity and purification is not required.

The substituted cyclohexene (2) is polymerized to produce a polymer (3) in high yield. This polymerization is conveniently carried out with bis-phenol A and excess anhydrous potassium carbonate in dimethylacetamide and toluene. The polymer (3) is formed as a white fibrous polymer.

Dehydrogenation of polymer (3) produces the fully aromatized polyketones (4) within formula (I). The dehydrogenation may be carried out with 10% Pd/C and a catalytic amount of elemental sulfur in diphenyl ether under reflux conditions; the polyketone is typically produced in 30 hours in 85% yield.

Reaction of polyketone (4) with benzylamine produces the isoquinoline polymer (5) within formula (I), as shown in Scheme 1.

Reaction of polyketone (4) with hydrazines produces a corresponding polyphthalazine within formula (I).

The properties of the polymers produced in Scheme 1 are set out in Table I below:

TABLE 1

| | | General Properties of Polymer 3,4,5. | | | | |
|---|---|---|---|---|---|---|
| Polymer | Yield wt % | $\eta\text{inh}^a$ (dL/g) | Tg (°C.) | $\overline{M}w^b$ | $\overline{M}n^b$ | $\overline{M}w/Mn$ | Film$^c$ |
| 3 | 95 | 0.44 | 190 | 38 062 | 16 201 | 2.3 | Tough |
| 4$^d$ | 85 | 0.36 | 160 | 24 532 | 8 761 | 2.8 | Tough |
| 4$^e$ | 95 | 0.48 | 180 | 22 432 | 8 337 | 2.6 | Tough |
| 5 | 98 | 0.38 | 225 | 34 632 | 11 942 | 2.9 | Brittle |

$^a$The inherent viscosities were measured at a concentration of 0.5 g/dL in chloroform at 25° C.
$^b$Determined by GPC (based on polystyrene standards).
$^c$Films were cast in methylene chloride at 25° C.
$^d$Polyketone polyether 4 obtained from polymer 3.
$^e$Polymer 4 obtained from direct polymerization of monomer 7.

The synthesis of polymer (4) can also be carried out by direct conversion of the substituted cyclohexene (2) to the O-dibenzoylbenzene monomer (7) as illustrated in Scheme 2:

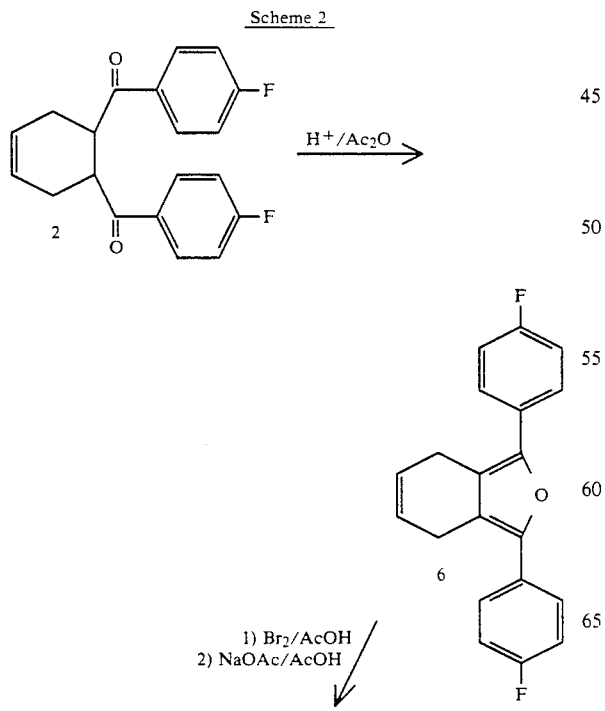

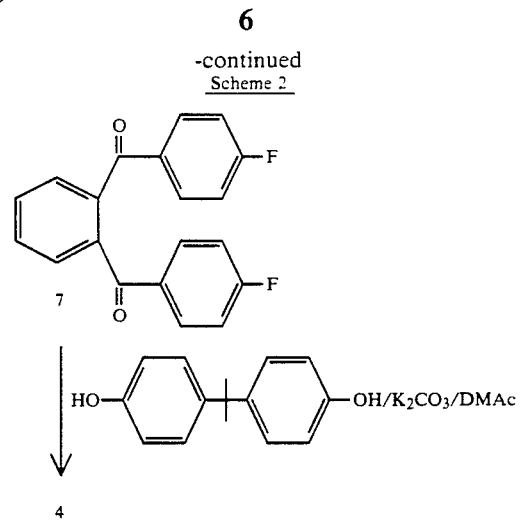

The reaction of the substituted cyclohexene (2) with a few drops of sirupy phosphoric acid in acetic anhydride gives the dihydroisobenzofuran (6) in quantitative yield (R. Adams & M. H. Gold, J.A.C.S., 1940, 62, 56).

Treatment of the dihydroisobenzofuran (6) with two moles of bromine followed by sodium acetate in acetic acid gives di(p-fluorobenzoyl)benzene (7) in high yield (R. Adams et al, J. Am. Chem. Soc. 1940, Vol. 62, pages 1233 and 2038).

Polymerization of the di-(p-fluorobenzoyl)benzene (7) with bis-phenol A and excess anhydrous potassium carbonate in dimethylacetamide and toluene gives the polyether polyketone (4) in high yield of about 95%.

By utilizing 1,4-diphenylbutadiene instead of butadiene in the reaction with di-(p-fluorobenzoyl)ethylene polyketones of formula (I) are produced in which $A_1$ and $A_4$ are phenyl.

Polyketones of formula (I) in which $A_1$, $A_2$, $A_3$ and $A_4$ are all phenyl are prepared employing the modification illustrated in Scheme 3:

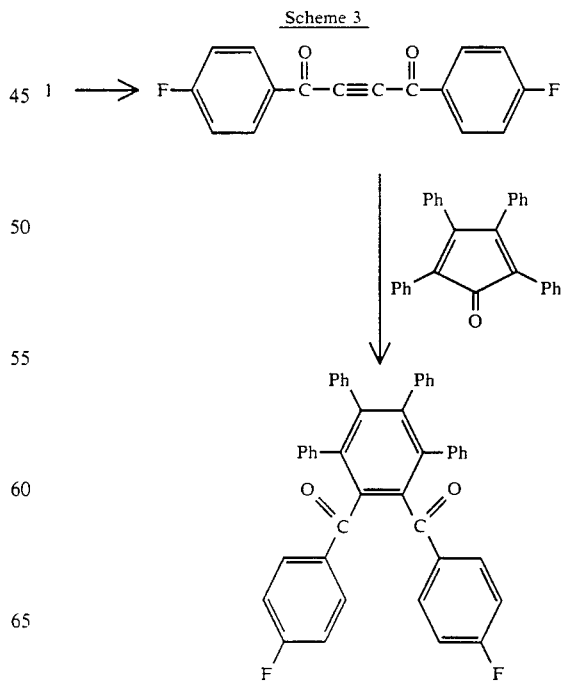

the product being polymerized with bis-phenol A as described for compounds (2) and (7).

The starting material di-(p-fluorobenzoyl)ethylene (1) can be obtained by reaction of fluorobenzene and aluminium chloride with fumaryl chloride (U.S. Pat. No. 4,130,409).

As indicated above polyphthalazines and polyisoquinolines within formula (I) are synthesized by direct reaction of the polyketones of formula (I) with hydrazine or benzylamine, respectively as illustrated in Scheme 4:

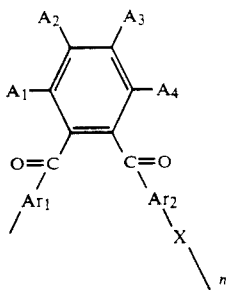

Scheme 4

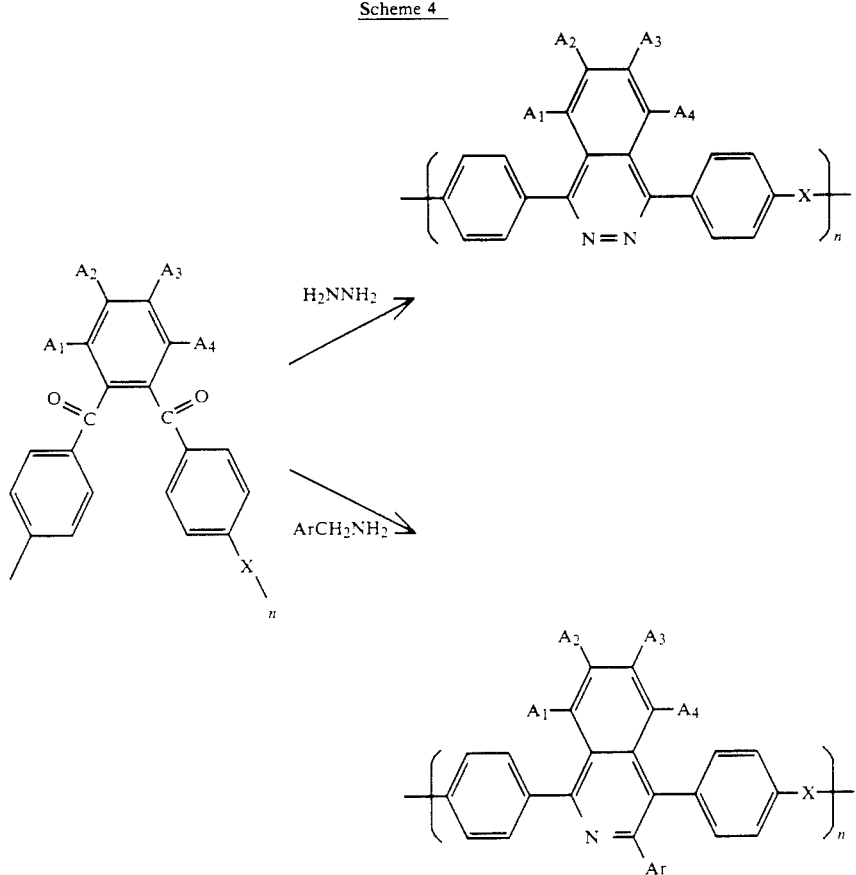

By controlling the amount of reagents in the reaction mixture copolymers of the original polyketones and the phthalazine or isoquinoline units are produced.

Alternatively the di-(p-fluorobenzoyl)benzene (7) and its substituted derivatives can be cyclized directly to the corresponding phthalazine monomer and the fluoro groups are sufficiently activated by the heterocyclic ring to allow polymerization directly with bisphenates to the corresponding polyphthalazines.

Di-(p-chlorobenzoyl)benzene, the chloro analog of (7) can be polymerized directly with a nickel catalyst to produce the polyketone (I), where X is a single bond.

Thus generally stated polyketones of formula (IA):

within the scope of formula (I) are produced by dehydrogenation of a polymer of formula (V):

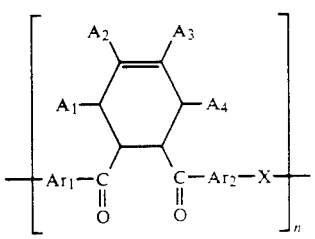

wherein $A_1$, $A_2$, $A_3$ $A_4$, $Ar_1$, Ar, X and n are as defined hereinbefore.

Furthermore polyphthalazines of formula (IB):

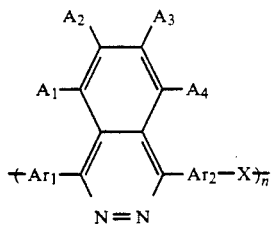

wherein $A_1$, $A_2$, $A_3$, $A_4$, $Ar_1$, $Ar_2$, X and n are as defined above, are produced by reacting a polyketone of formula (IA), as defined above, with hydrazine.

Still further, polyisoquinolines of formula (IC):

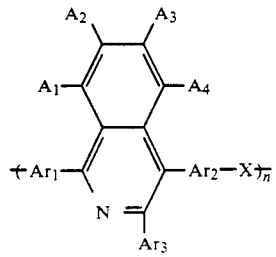

wherein $A_1$, $A_2$, $A_3$, $A_4$, $Ar_1$, $Ar_2$, X and n are as defined above, are produced by reacting a polyketone of formula (IA), as defined above, with a benzylamine of formula (IV):

$Ar_3-CH_2-NH_2$ in which $Ar_3$ is as defined hereinbefore.

The polyphthalazines of formula (IB) above are also produced by reacting a phthalazine monomer of formula (XIII):

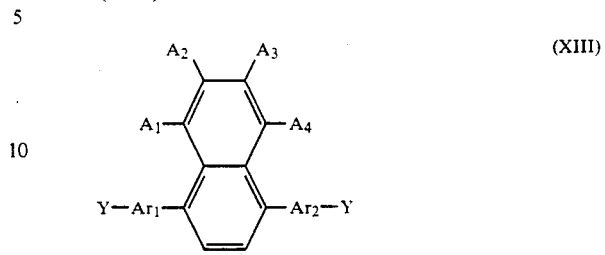

in which A, $A_2$, $A_3$, $A_4$ $Ar_1$ and $Ar_2$ are as defined above and each Y is a halogen atom, especially fluorine, chlorine or bromine, with a compound of formula:

$$MX_1M \qquad (XIV)$$

in which $X_1$ is $-O-R-O$, S or $-S-R-S$ wherein R is as defined above and M is an alkali metal, for example, sodium or potassium.

Phthalazine monomers of formula (XIII) in which Y is chlorine and bromine can be polymerized to produce the polyphthalazines of formula (IB) above, in which X is a single bond. This polymerization is suitably carried out in the presence of a nickel catalyst generated from nickel chloride with zinc.

Properties

The properties of polyketones, polyphthalazines and polyisoquinolines of formula (I) are set out in Tables, 2, 3 and 4, respectively.

TABLE 2

| | POLYKETONES | | | | | | | | |
|---|---|---|---|---|---|---|---|---|---|
| R | A1 | A2 | A3 | A4 | Tg deg. C. | Mwx 10000 | Mnx 10000 | inh. visc | film |
| OPhO | H | H | H | H | 185 | 2.12 | 1.11 | 0.43 | flex |
| OPhO | Ph | H | H | Ph | 240 | 2.24 | 1.04 | 0.35 | flex. |
| OPhO | Ph | Ph | Ph | Ph | 275 | 2.56 | 1.6 | 0.49 | flex |
| OPhPhO | H | H | H | H | 190 | 2.3 | 1.1 | 0.42 | flex |
| OPhPhO | Ph | H | H | Ph | 240 | 7.67 | 3.67 | 0.56 | flex. |
| OPhPhO | Ph | Ph | Ph | Ph | 290 | 4.34 | 2.53 | 0.73 | flex. |
| OPhC(CH3)2PhO | H | H | H | H | 180 | 3.24 | 1.71 | 0.48 | flex. |
| OPhC(CH3)2PhO | Ph | H | H | Ph | 220 | 8.54 | 5.16 | 0.65 | flex. |
| OPhC(CH3)2PhO | Ph | Ph | Ph | Ph | 265 | 4.4 | 2.73 | 0.47 | flex |

TABLE 3

| | POLYPHTHALAZINES | | | | | | | | |
|---|---|---|---|---|---|---|---|---|---|
| R | A1 | A2 | A3 | A4 | Tg deg. C. | Mwx 10000 | Mnx 10000 | inh. visc | film |
| OPhO | H | H | H | H | 260 | — | — | — | — |
| OPhO | Ph | H | H | Ph | 270 | 5.01 | 1.62 | 0.53 | flex. |
| OPhO | Ph | Ph | Ph | Ph | 295 | 15.3 | 6.32 | 0.61 | flex |
| OPhPhO | H | H | H | H | 255 | — | — | — | — |
| OPhPhO | Ph | H | H | Ph | 300 | 18.23 | 5.52 | 0.93 | flex. |
| OPhPhO | Ph | Ph | Ph | Ph | 340 | 40.2 | 9.56 | 1.21 | flex |
| OPhC(CH3)2PhO | H | H | H | H | 235 | 4.79 | 1.91 | 0.72 | flex. |
| OPhC(CH3)2PhO | Ph | H | H | Ph | 250 | 12.52 | 6.21 | 0.89 | flex. |
| OPhC(CH3)2PhO | Ph | Ph | Ph | Ph | 285 | 16.23 | 3.85 | 0.64 | flex |

TABLE 4

| | POLYISOQUINOLINES | | | | | | | | |
|---|---|---|---|---|---|---|---|---|---|
| R | A1 | A2 | A3 | A4 | Tg deg. C. | Mwx 10000 | Mnx 10000 | inh. visc | film |
| OPhO | H | H | H | H | 220 | — | — | — | — |
| OPhO | Ph | H | H | Ph | 260 | 6.05 | 1.44 | 0.51 | flex |
| OPhO | Ph | Ph | Ph | Ph | 290 | 20.8 | 5.34 | 0.58 | flex |
| OPhPhO | H | H | H | H | 230 | — | — | — | — |
| OPhPhO | Ph | H | H | Ph | 275 | 15.32 | 5.17 | 0.88 | flex |

TABLE 4-continued

| | | | | | POLYISOQUINOLINES | | | | |
|---|---|---|---|---|---|---|---|---|---|
| R | A1 | A2 | A3 | A4 | Tg deg. C. | Mwx 10000 | Mnx 10000 | inh. visc | film |
| OPhPhO | Ph | Ph | Ph | Ph | 320 | 18.09 | 3.77 | 0.98 | flex |
| OPhC(CH3)2PhO | H | H | H | H | 225 | 4.83 | 2.1 | 0.59 | flex. |
| OPhC(CH3)2PhO | Ph | H | H | Ph | 235 | 9.32 | 3.32 | 0.68 | flex. |
| OPhC(CH3)2PhO | Ph | Ph | Ph | Ph | 280 | 22.5 | 5.22 | 0.65 | flex |

The Tg of the polyketone (4) produced in Scheme 2 is higher than the Tg of the corresponding meta polyketone which has a Tg of 153° C. (see Hergenrother et al hereinbefore) and higher than that of the corresponding para polymer which has a Tg of 165° C. (see R. Johnson et al hereinbefore). The higher Tg of the ortho polymer as compared with its meta and para isomers likely results from restricted rotation in the ortho isomer. The Tgs of the polymers (I) increase with increasing substitution of the aromatic nuclei, for example when A1, A2, A3, A4 are all phenyl there is an increase in Tg of about 80° to 90° C. as compared with the polymers in which A1, A2, A3 and A4 are all hydrogen.

Replacing the flexible bisphenol A moiety by more rigid hydroquinone or 4,4'-biphenol moieties also increases the Tg. With only a carbon-carbon linkage between the monomer units a greater rise in Tg is obtained.

The most dramatic changes in properties occur when the ketone polymers are cyclized to the polyphthalazines or polyisoquinolines. Structurally this results in a significant straightening of the chain. In the polymers with only a carbon-carbon linkage between the monomer units this would convert the relatively flexible chain to a rigid rod structure. The change in structure manifests itself not only in a significant increase in glass transition temperature but a large increase in the solution viscosity and a large increase in the apparent molecular weight as measured by gel permeation chromatography. In this case the polymers are compared to a polystyrene standard and the rigid molecules would take up more free volume and hence appear to be higher molecular weight since GPC separates molecules on the basis of size exclusion.

All of the polymers (I) synthesized are amorphous materials, are soluble in solvents such as chloroform at room temperature and can be cast into tough, transparent, flexible films. A wide range of glass transition temperatures are available, from 180° C. to 340° C., or higher.

Thus the polymers (I) of the invention have the particular advantages that their solubility in organic solvents permits them to be readily cast from solution to produce films, and their high Tg renders them suitable for high temperature applications.

Epoxides

Epoxidized polymers can also be formed. Thus polymer (3) in Scheme 1 has been epoxidized with hydrogen peroxide and a catalyst, for example a quaternary ammonium tetrakis(dipperoxotungsto)phospate(3-) catalyst, in accordance with Scheme 5:

Scheme 5

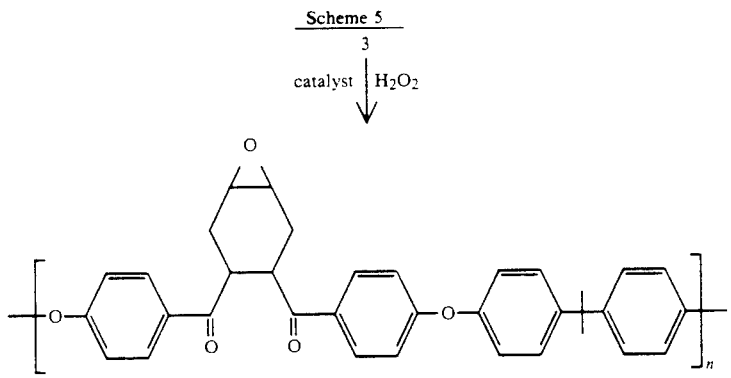

Furthermore, polymers with a smaller number of epoxide units are produced by copolymerizing the substituted cyclohexene (2) of Scheme 2 to produce copolymers with a lesser amount of unsaturation for epoxidation.

Epoxidized polymers of the type are cured by reaction with amines to yield insoluble polymers which serve as matrices for advanced composites. They can also be cured photochemically in the presence of onium salts, for example triphenylsulfonium hexafluoroarsenate, as catalysts which on irradiation yield strong acids which effect a cure where the polymer films are exposed to light. These materials are useful in microelectronics as high temperature resists.

EXAMPLES

Example 1

Di-(p-fluorobenzoyl)ethylene 1

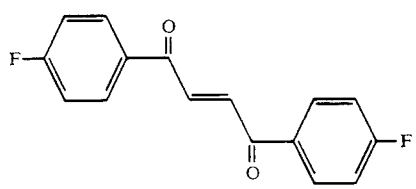

To a solution of fluorobenzene (0.52 mols, 50 g, 48.83 mL) in carbon disulfide (500 mL) was added aluminium chloride (0.651 mmol, 86.8 g). The resulting suspension was gently refluxed under an atmosphere of nitrogen. Fumaryl chloride (0.26 mols, 28.2 mL) was added over a period of 15-20 minutes. The resulting dark orange reaction mixture was refluxed for 18 h and the residue was poured into crushed ice (1 Kg) and concentrated hydrochloric acid (15.0 mL). The semi-solid was filtered off, washed with ether and ethanol, digested in ethanol, and recrystallized from ethyl acetate/ethanol to give pale yellow needles of compound 1 in 96% yield, m.p. 115°–116° C. $^1$H NMR: 7.14–7.18 (t, 2H, $J_{meta}=1.9$ Hz, $C_6H_4$), 7.96 (s, 2H, CH=CH), 8.05–8.12 (q, 6H, J=2.2 Hz, $C_6H_4$); ms m/e (Cl with $NH_3$), 290($NH_3$+H+M), 273(M+1), 272(M); HRMS m/e calcd for $C_{16}H_{10}O_2F_2$ 273.0727, found 273.0727.

Example 2

Di-(p-chlorobenzoyl)ethylene 2

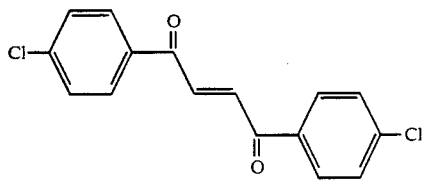

The above procedure was used to synthesize the chloro anologue. The yield was 96% after recrystallization from ethanol and ethyl acetate, the m.p. 151°–153° C.

Example 3

Diels Alder Adduct; Fluoro-4,5-dibenzoylcyclohexene 3

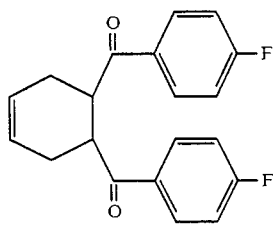

To a cooled solution of 1,3-butadiene (22.1 mmol, 1.19 g) in 150 mL of benzene was added di-(p-fluorobenzoyl)ethylene 1 (11.0 mmol, 3 g). The intensely yellow coloured reaction mixture was heated at reflux in a pressure bomb until a colourless mixture resulted (10–12 h). The reaction mixture was concentrated under reduced pressure and the solid was recrystallized from ethanol to give a white crystalline compound 3 in 100% yield with a m.p. of 118°–120° C.

Example 4

Diels Alder Adduct-Chloro-4,5-Dibenzoyl 4

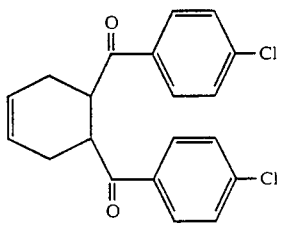

The above reaction for the formation of compound 3 was repeated in the synthesis of chloro cyclohexane 4. The yield was 100% and m.p. 120°–121° C.

Example 5

Conversion of Ortho-Diaroyl Cyclohexenes to the Corresponding Dihydroisobenzofurans 5 and 6

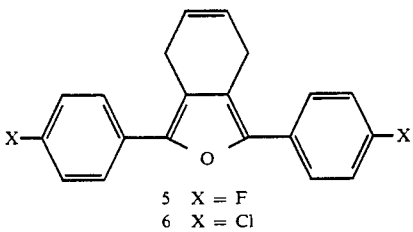

5 X = F
6 X = Cl

To a reaction mixture of 25 g of 4,5-di-p-fluorobenzoylcyclohexene 3 in 200 mL of hot acetic anhydride was added 0.5 g of 86% sirupy phosphoric acid. The reaction mixture was refluxed for ten minutes and upon cooling the insoluble furan crystallized immediately to give a quantitative yield of difluorodihydroisobenzofuran 5.

Example 6

In a similar fashion dichlorohydroisobenzofuran 6 was synthesized from chloro-4,5-dibenzoylcyclohexene 4.

Example 7

Conversion of Diaryl-dihydroisobenzofurans to Corresponding Ortho-Dibenzoylbenzenes 7 and 8

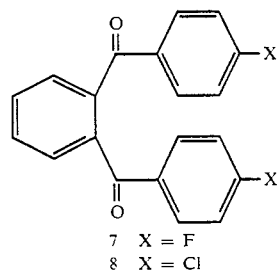

7 X = F
8 X = Cl

To a boiling solution of difluorohydroisobenzofuran 5 (35.4 mmol, 10.9 g) in glacial acetic acid (500 mL) was added a solution of bromine (70.8 mmol, 11.3 mL) in 60 mL of glacial acetic acid. The reaction mixture was refluxed for fifteen minutes until the bromine was completely absorbed then sodium acetate (283.2 mmol, 23.23 g) was added and reflux was continued for another fifteen minutes. To the refluxing mixture was added water (150 mL) and then it was allowed to cool slowly for several hours. The white solid was filtered and recrystallized from ethanol to give, quantitatively, ortho-difluorobenzoyl benzene 7, m.p. 90°–91° C.

Example 8

In a similar fashion ortho-dichlorobenzoyl benzene 8 (100%, m.p. 160°–162° C.) was synthesized from dichlorohydroisobenzofuran.

Example 9

Synthesis of Ortho-DifluoroDiphenylDiaroylCyclohexene 9 And Ortho-DichloroDiphenylDiaroylCyclohexene 10

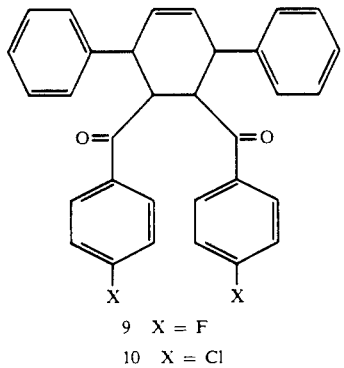

9  X = F
10 X = Cl

To a solution of di-(p-fluorobenzoyl)ethylene 1 (73.5 mmol, 20 g) in ethyl benzene (500 mL) was added trans, trans, 1,4-diphenyl-1,3-butadiene (73.5 mmol, 15.16 g). The reaction mixture was refluxed for 18 h, cooled, concentrated to give a white granular solid. Upon recrystallization from ethanol, ortho-difluoro-diphenyl-diaroylcyclohexene 9 was isolated as fine needle-like white crystals in quantitative yield, m.p. 170°–172° C.

Example 10

In a similar fashion the synthesis of ortho-dichlorodiphenyldiaroylcyclohexene 10, m.p. 170°–172° C. was synthesized.

Example 11 and 12

Conversion of O-Diaroyl Cyclohexenes 9 and 10 to the Corresponding Dihydroisobenzofurans 11 and 12

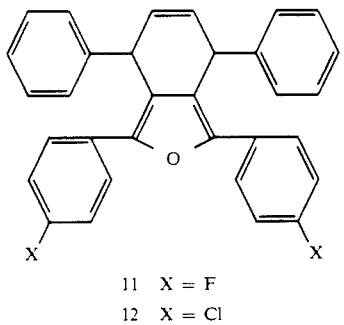

11 X = F
12 X = Cl

The conversion of ortho-diaroyl cyclohexenes 9 and 10 to the corresponding dihydroisobenzofurans 11 and 12 was done quantitatively (m.p. 250°–251° C., m.p. 237°–239° C., respectively) and in a similar fashion as the synthesis of isobenzofurans 5 and 6.

Example 13 and 14

Conversion of Diaroyl-dihydroisobenzofurans 11 and 12 to Corresponding ortho-Dibenzoylbenzenes 13 and 14

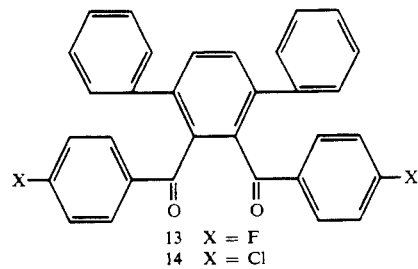

13 X = F
14 X = Cl

The same procedure was used for the conversion of diaryl-dihydroisobenzofurans 11 and 12 to the corresponding ortho-dibenzoylbenzenes 13 and 14 as was done for the conversion of diaryldihydroisobenzofuran 5 and 6 to their corresponding ortho-dibenzoylbenzenes 7 and 8. The compounds 13 and 14 were isolated in quantitative yield with m.p. of 172°–174° C. and 180°–182° C., respectively.

Example 15 and 16

Synthesis of Dibenzoylethylene dibromide 15 and 16

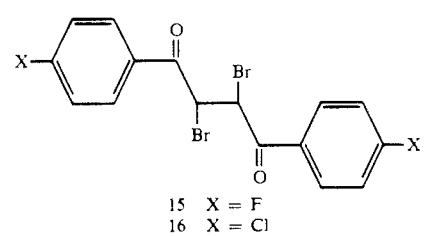

15 X = F
16 X = Cl

Di-(p-fluorobenzoyl)ethylene 1 (25.7 mmol, 7 g) was added to carbon tetrachloride (200 mL) to which was added a solution of bromine (25.7 mmol, 1.32 mL) in carbon tetrachloride (5 mL). The reaction mixture was stirred under an atmosphere of nitrogen for thirty minutes and concentrated under reduced pressure to give a white solid. Recrystallization of the solid from a mixture of petroleum ether and ethyl acetate (2/1) gave quantitatively difluorodibenzoylethylene dibromide 15. A similar reaction was done to obtain the dichlorodibenzoylethylene dibromide 16.

Example 17 and 18

Synthesis of Dibenzoylacetylene 17 and 18

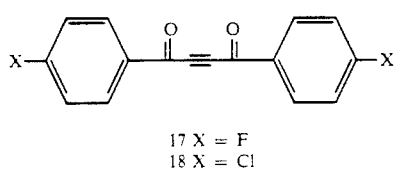

17 X = F
18 X = Cl

To a solution of difluorodibenzoylethylene dibromide 15 (16.3 mmol, 7.0 g) in acetone (100 mL), under an atmosphere of nitrogen was added triethylamine (39.2 mmol, 5.5 mL). Upon refluxing the reaction mixture for fifteen minutes, the quaternary salt was filtered, and the filtrate concentrated under reduced pressure. The product was recrystallized from ethanol to give difluorodibenzoylacetylene 17 in 90% yield.

A similar reaction was repeated for the synthesis of the dichlorodibenzoylacetylene 16

Example 19 and 20

Synthesis of Tetraphenyl ortho-Dibenzoylbenzenes 19 and 20

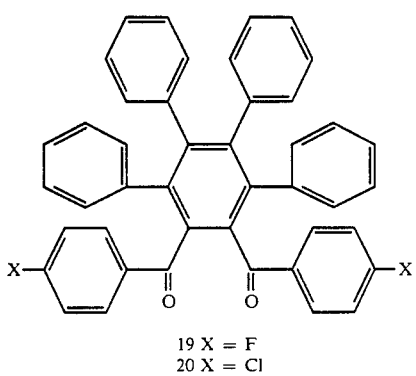

19 X = F
20 X = Cl

Difluoroacetylene 17 (18.6 mmol, 5.0 g) and tetraphenylcyclopentadienone (18.6 mmol, 7.15 g) in benzophenone (70 g) were refluxed for 18 h under an atmosphere of nitrogen. The reaction mixture was cooled to 30° C. and poured into a large volume (300 mL) of methanol. The tan precipitate was washed with methanol (2×25 mL) and refluxed in benzene/charcoal to give a white crystalline compound tetraphenyl ortho-difluorodibenzoylbenzene 19 in 89% yield, m.p. 318°-320° C.

Similarily, tetraphenyl ortho-dichlorodibenzoylbenzene 20 was synthesized.

Example 21, 22 and 23

Synthesis of Phthalazine Monomers 21, 22, 23 from ortho-difluorodibenzoylbenzene monomers 7, 13, and 19

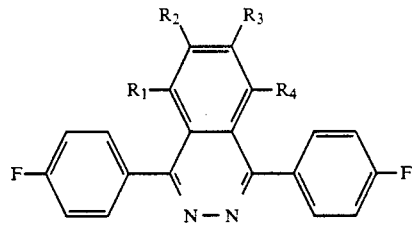

21 $R_1 = R_2, R_3, R_4 = H$
22 $R_1 = R_4 = C_6H_5; R_2 = R_3 = H$
23 $R_1 = R_2 = R_3 = R_4 = C_6H_5$

To ortho-difluorodibenzoylbenzene 7 (16 mmol, 500 mg) in acetic acid (10 mL) was added hydrazine hydrate (3 g). The reaction mixture was refluxed for 1 h, cooled and the precipitate filtered. The white solid was recrystallized from ethanol to give quantitatively difluorodiphenyl phthalazine 21, m.p. 219°-221° C.

The above procedure was employed for the synthesis of phenylated phthalazine monomers 22 and 23.

General Synthesis Of Polyetherpolyphenylketone 24

Example 24

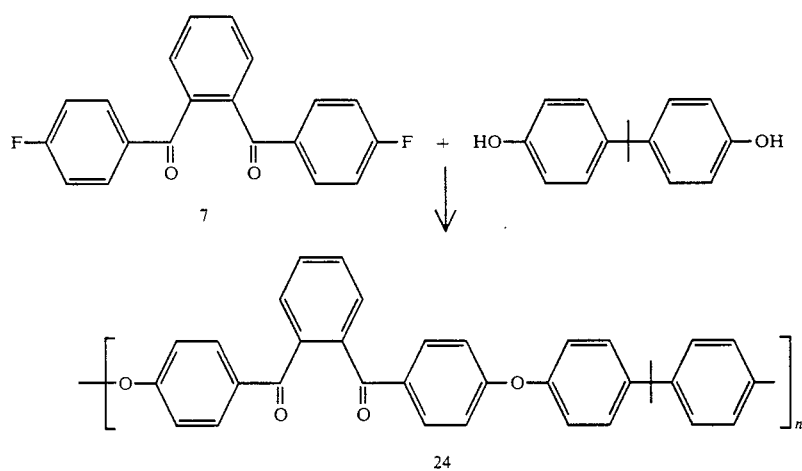

A typical synthesis of a polyether polyphenyl ketone was conducted in a three-neck flask equipped with a nitrogen inlet, thermometer, Dean-Stark trap and condenser. A detailed synthetic procedure designed to prepare a polyether polyphenyl ketone based on orthodifluorodibenzoylbenzene monomer 7 is provided. The flask was charged with (6.21 mmol, 2 g) of monomer 7, bisphenol (BPA) (6.21 mmol, 1.42 g) and N,N-dimethylacetamide (10 mL). Toluene (3 mL) was added, followed by potassium carbonate (6.21 mmol, 857 mg). Note that potassium carbonate cannot be used in excess in the case of polymerization of the orthodifluorodibenzoylbenzene monomer 7, however for the other two orthodifluorodibenzoylbenzene monomers 13 and 19, at least 2 to 3 fold excess of base can be readily used. The reaction mixture was then heated until the toluene began to reflux. An optimum reflux temperature range was achieved between 140°-150° C. Toluene was periodically removed from the Dean-Stark trap and replaced with dry toluene to ensure dehydration. The reaction was maintained at 145° C. until the presence of water was no longer observed in the Dean-Stark trap, which may take 1-2 h. Upon dehydration, the temperature was slowly increased to 165° C., and the toluene was removed through the Dean-Stark trap. The reaction mixture was heated at 165° C. for approximately 1 h. Completion or near completion was qualitatively estimated by the point where the viscosity increased dramatically. The reaction mixture was cooled, diluted with N,N-dimethylacetamide and several drops of weak acid (e.g., acetic acid) were added to neutralize phenoxide end groups. The polymer solution was then coagulated in about 10X volume of methanol and filtered, redissolved in chloroform, and filtered hot through a thin layer of Celite. The polymer 24 was then dried in a vacuum oven (80° C.) to a constant weight. The yield was essentially quantitative.

Examples of other polyketones with the structure shown are given in Table 1.

General Synthesis of Polyisoquinolines from PolyetherPolyphenylketone 24

Example 33

A typical synthesis of a polyisoquinoline polymer was conducted under an atmosphere of nitrogen. To a solution of polyether polyphenylketone 24 (1.18 mmol, 600 mg) in chlorobenzene (20 mL) was added benzylamine (5.9 mmol, 0.65 mL) and 1,8-diazabicyclo[5.4.0]undec-7-ene (5.9 mmol, 0.89 mL).

TABLE 1

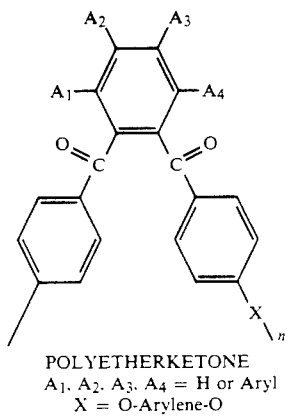

POLYETHERKETONE
$A_1, A_2, A_3, A_4$ = H or Aryl
X = O-Arylene-O

POLYKETONES

| EXAMPLE | R | A1 | A2 | A3 | A4 | Tg deg. C. | Mw × 10000* | Mn × 10000* | inherent viscosity** | film |
|---|---|---|---|---|---|---|---|---|---|---|
| 24 | OPhC(CH3)2PhO | H | H | H | H | 180 | 3.24 | 1.71 | 0.48 | flexible |
| 25 | OPhC(CH3)2PhO | Ph | H | H | Ph | 220 | 8.54 | 5.16 | 0.65 | flexible |
| 26 | OPhC(CH3)2PhO | Ph | Ph | Ph | Ph | 265 | 4.4 | 2.73 | 0.47 | flexible |
| 27 | OPhO | H | H | H | H | 185 | 2.12 | 1.11 | 0.43 | flexible |
| 28 | OPhO | Ph | H | H | Ph | 240 | 2.24 | 1.04 | 0.35 | flexible |
| 29 | OPhO | Ph | Ph | Ph | Ph | 275 | 2.56 | 1.6 | 0.49 | flexible |
| 30 | OPhPhO | H | H | H | H | 190 | 2.3 | 1.1 | 0.42 | flexible |
| 31 | OPhPhO | Ph | H | H | Ph | 240 | 7.67 | 3.67 | 0.56 | flexible |
| 32 | OPhPhO | Ph | Ph | Ph | Ph | 290 | 4.34 | 2.53 | 0.73 | flexible |

*by Gel permeation chromatography; polystyrene standards
**0.5 g/dl; CHCl3 @ 25 deg. C.

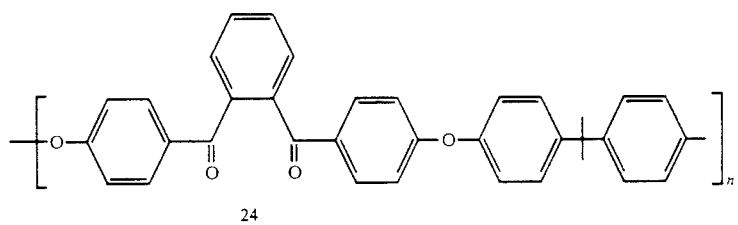

24

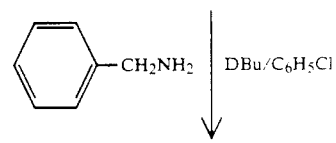

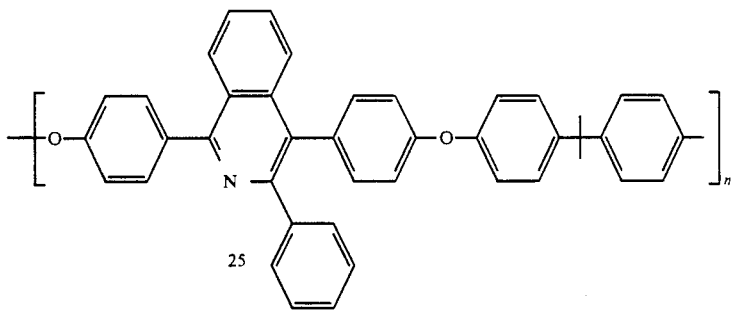

25

The reaction mixture was refluxed for a period of 30 h, cooled, concentrated under reduced pressure, and dissolved in chloroform. The polymer solution was filtered hot through Celite and poured into a large amount of methanol. The polyisoquinoline polymer 25 was collected as a pale yellow fibrous solid, washed with methanol, reprecipitated, and dried in vacuo at 80° C. for 24 h. The yield was quantitative.

Examples of other polyisoquinolines with the structure shown are given in Table 2.

for the synthesis of polyisoquinoline 25. To a solution of polyetherpolyphenylketone 24 (1.18 mmol, 600 mg) in chlorobenzene (20 mL) was added glacial acetic acid (12 mmol, 0.70 mL) followed by a slow addition of hydrazine (6 mmol, 0.30 mL) The reaction mixture was left to reflux for 15 h. After this period, $^1$H nmr studies indicated the reaction had undergone 50% completion. A copolymer of polyphthalazine-polyetherpolyketone was isolated. Upon further reflux (15 h), the reaction had reached completion. The polymer solution was

TABLE 2

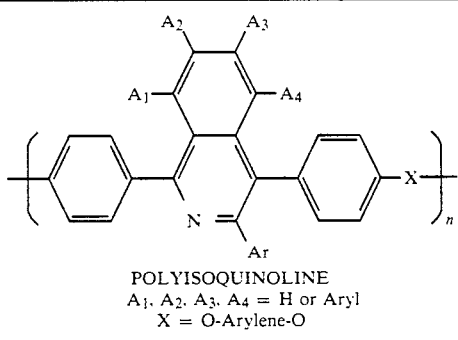

POLYISOQUINOLINE
$A_1, A_2, A_3, A_4 = H$ or Aryl
X = O-Arylene-O

| EXAMPLE | R | A1 | A2 | A3 | A4 | Tg deg. C. | Mw × 10000* | Mn × 10000* | inherent viscosity** | film |
|---|---|---|---|---|---|---|---|---|---|---|
| 33 | OPhC(CH3)2PhO | H | H | H | H | 225 | 4.83 | 2.1 | 0.59 | flexible |
| 34 | OPhC(CH3)2PhO | Ph | H | H | Ph | 235 | 9.32 | 3.32 | 0.68 | flexible |
| 35 | OPhC(CH3)2PhO | Ph | Ph | Ph | Ph | 280 | 22.5 | 5.22 | 0.65 | flexible |
| 36 | OPhO | H | H | H | H | 220 | — | — | — | — |
| 37 | OPhO | Ph | H | H | Ph | 260 | 6.05 | 1.44 | 0.51 | flexible |
| 38 | OPhO | Ph | Ph | Ph | Ph | 290 | 20.8 | 5.34 | 0.58 | flexible |
| 39 | OPhPhO | H | H | H | H | 230 | — | — | — | — |
| 40 | OPhPhO | Ph | H | H | Ph | 275 | 15.32 | 5.17 | 0.88 | flexible |
| 41 | OPhPhO | Ph | Ph | Ph | Ph | 320 | 18.09 | 3.77 | 0.98 | flexible |

*by Gel permeation chromatography; polystyrene standards
*0.5 g/dl; CHCl3 @ 25 deg. C.

General Synthesis of Polyphthalazines from Polyetherpolyketones

Example 42.

A typical synthesis of a polyphthalazine was conducted under an atmosphere of nitrogen. The same polymer batch of polyetherpolyketone 24 was used as concentrated under reduced pressure, dissolved in chloroform, filtered hot through Celite and poured into a large amount of methanol. The polyphthalazine polymer 26 was collected as yellow fibrous solid, washed with methanol, reprecipitated, and dried in vacuo at 80° C. for 24 h. The yield was quantitative.

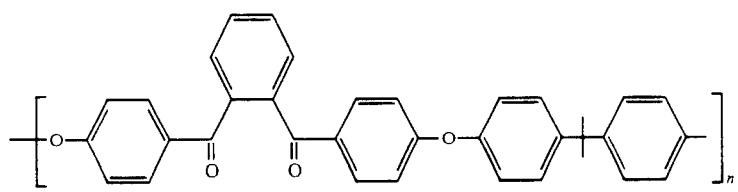

↓ H₂NNH₂.H₂O/AcOH/C₆H₅

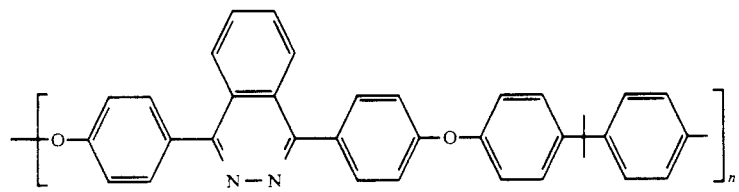

Examples of other polyphthalazines with the structure shown are given in Table 3.

TABLE 3

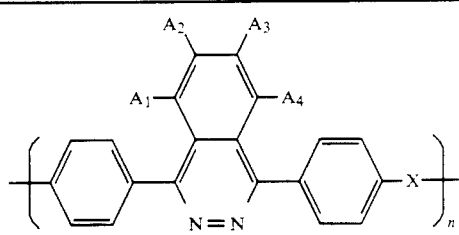

POLYPHTHALAZINE
A₁, A₂, A₃, A₄ = H or Aryl
X = O-Arylene-O

| EXAMPLE | R | A1 | A2 | A3 | A4 | Tg deg. C. | Mw × 10000* | Mn × 10000* | inherent viscosity** | film |
|---|---|---|---|---|---|---|---|---|---|---|
| 43 | OPhC(CH3)2PhO | H | H | H | H | 235 | 4.79 | 1.91 | 0.72 | flexible |
| 44 | OPhC(CH3)2PhO | Ph | H | H | Ph | 250 | 12.52 | 6.21 | 0.89 | flexible |
| 45 | OPhC(CH3)2PhO | Ph | Ph | Ph | Ph | 285 | 16.23 | 3.85 | 0.64 | flexible |
| 46 | OPhO | H | H | H | H | 260 | — | — | — | — |
| 47 | OPhO | Ph | H | H | Ph | 270 | 5.01 | 1.62 | 0.53 | flexible |
| 48 | OPhO | Ph | Ph | Ph | Ph | 295 | 15.3 | 6.32 | 0.61 | flexible |
| 49 | OPhPhO | H | H | H | H | 255 | — | — | — | — |
| 50 | OPhPhO | Ph | H | H | Ph | 300 | 18.23 | 5.52 | 0.93 | flexible |
| 51 | OPhPhO | Ph | Ph | Ph | Ph | 340 | 40.2 | 9.56 | 1.21 | flexible |

*by Gel permeation chromatography; polystyrene standards.
*0.5 g/dl; CHCl3 @ 25 deg. C.

General Synthesis of Polyphthalazines from Phthalazine Monomers

Example 52

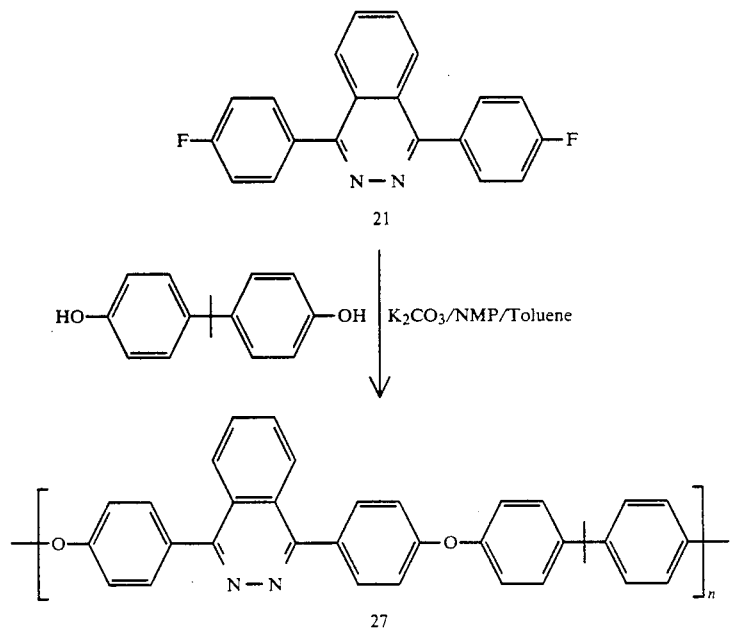

Another route to the synthesis of polyphthalazines is directly from phthalazine monomers. As an illustration, a detailed synthetic procedure designed to prepare a polyphthalazine polymer 27 based on the phthalazine monomer 21 is provided. A three-neck round bottom flask equipped with a nitrogen inlet, Dean-Stark, and condensor was charged with phthalazine monomer 21 (6.4 mmol, 2.0 g) and bisphenol (BPA) (6.4 mmol, 1.45 g). Under an inert atmosphere 1-methyl-2-pyrrolidinone (15 mL) and toluene (3.5 mL), followed by anhydrous potassium carbonate (19.2 mmol, 2.6 g) was added. Note that potassium carbonate could readily be used in 2 to 3 fold excess. The reaction mixture was then heated until the toluene began to reflux. An optimum temperature range was reached at 145°-150° C. Toluene was periodically removed from the Dean-Stark trap and replaced with dry toluene to ensure dehydration. The reaction mixture was maintained at 145° C. until the presence of water was no longer observed in the Dean-Stark trap, which may take 1-2 h. During this stage of the reaction the solution underwent several colour changes. For example, during the initial formation of the phenoxide, a straw-yellow colour was observed, and as the refluxing proceeded, the colour changed to brown, green, and dark brown. Upon dehydration, the temperature was slowly increased to 180° C., and the toluene was removed through the Dean-Stark trap. The reaction mixture was heated at 180° C. for approximately 18-20 h. Completion of reaction was qualitatively estimated by the point where the viscosity increased dramatically. The reaction mixture was diluted with 1-methyl-2-pyrrolidinone and filtered hot to remove inorganic salts. The filtered solution was cooled, and several drops of weak acid acid (e.g., acetic acid) were added to neutralize phenoxide end groups. The polymer solution was then coagulated in methanol, filtered, redissolved in chloroform and precipitated in a large volume of methanol. The polymer 27 was then dried in a vacuum oven (80° C.) for 24 h. The yield was essentially quantitative.

Example 53

Polymerization of Diels-Alder Adduct: Difluoro-4,5-dibenzoylcyclohexene 3 to Polycyclohexenepolyetherketone 28

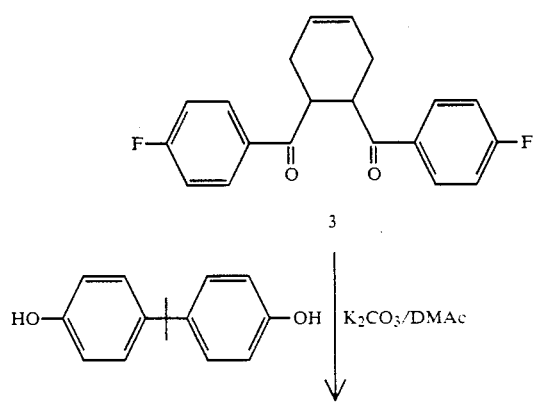

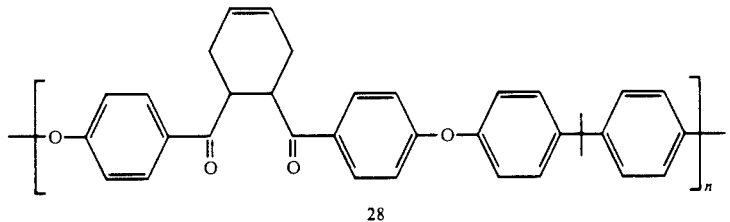

28

The synthesis of polycyclohexenepolyetherketone 28 was conducted in a three-neck flask equipped with a nitrogen inlet, Dean-Stark and condenser. A detailed synthetic procedure for its synthesis is as follows: The flask was charged with the monomer difluoro-4,5-difluoro-4,5-dibenzoylcyclohexene 3 (7.65 mmol, 2.48 g) and bisphenol (BPA) (7.65 mmol, 1.74 g) in N,N-dimethylacetamide (15 mL). Toluene (15 mL) was added, followed by anhydrous potassium carbonate (22.9 mmol, 3.2 g). The reaction mixture was then heated until toluene began to reflux. An optimum reflux temperature range was reached at 130° C. Toluene was periodically removed from the Dean-Stark trap to replace with dry toluene to ensure dehydration. The reaction mixture was maintained at 130° C. for 1-2 h at which point the viscosity increased enormously. The reaction mixture seemed to reach near completion or completion by the dramatic increase in viscosity and was then cooled, a few drops of acetic acid was added, and then diluted with toluene. The polymer solution was coagulated in a large amount of methanol, filtered, and washed with methanol. The white fibrous polymer 28 was redissolved in chloroform, hot filtered through Celite, reprecipitated into a large volume of methanol, filtered and dried in vacuo at 80° C. for 24 h. The yield was essentially quantitative.

Example 54

Epoxidation of Polycyclohexenepolyetherketone 28 to Polyepoxide 29 nitrogen, at 60° C. and to this was added the quaternary ammonium tetrakis(diperoxotungsto)phosphate(3-) catalyst (264 mg), followed by the addition of 30% hydrogen peroxide (1.02 mL). The solution became turbid after thirty minutes. The resulting two-phase reaction mixture was vigorously stirred for a period of 2 h at 60° C. The reaction mixture was then concentrated under reduced pressure at 50° C. to give a viscous solution. The polymer was precipitated in methanol, filtered to give a white fibrous polymer. Redissolving the polymer in chloroform and hot filtering through a layer of Celite gave again the fibrous white polymer. The epoxidized polymer 29 was then dried at 50° C. under vacuum for 24 h. Epoxidized polymer 29 was obtained in quantitative yield.

Example 55

Polymerization Reaction Involving Carbon-Carbon Coupling Reaction of Dichloro-Diphenyl-ortho-dibenzoylbenzene 14.

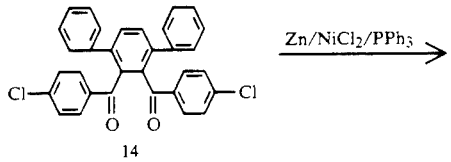

14

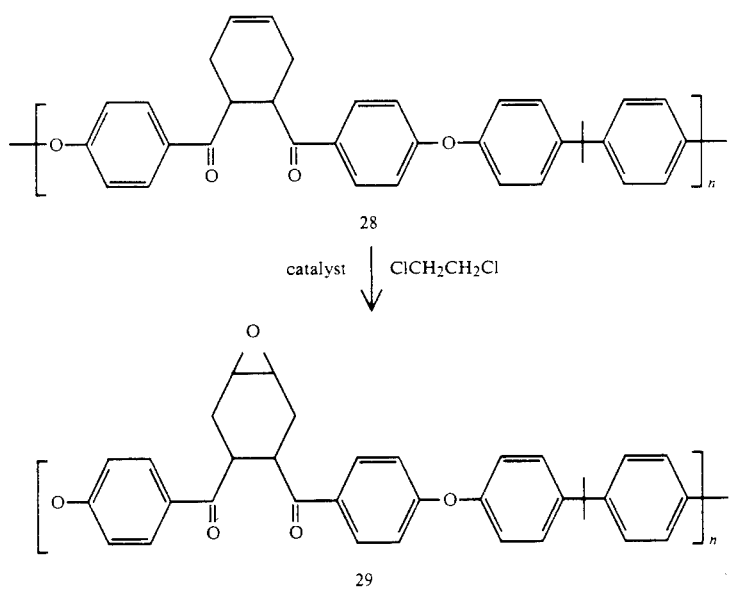

The epoxidation of the unsaturated polymer 28 involved: dissolving polymer 28 (2.00 mmol, 1.0 g) in 1,2-dichloroethane (40 mL), under an atmosphere of

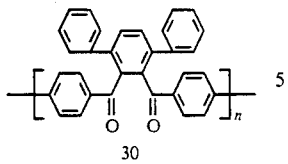

In a three neck round bottom flask under an atmosphere of nitrogen were placed nickel chloride (0.125 mmol, 16.2 mg), triphenylphosphine (0.25 mmol, 65.6 mg), bipyridine (0.125 mmol, 19.5 mg), zinc (7.75 mmol, 506 mg), and monomer dichlorodiphenyl-ortho-dibenzoylbenzene 14 (2.5 mmol, 1.27 g). The flask was evacuated and filled with nitrogen three times. Then, dry N,N-dimethylacetamide (3.0 mL) was added via a syringe through the serum cap. The mixture was stirred at 90° C. for 24 h. The reaction mixture became red-brown in 30 min. The resulting viscous mixture was diluted with N,N-dimethylacetamide (25 mL) and poured into a large amount of HCl/methanol. The polymer 30 was collected, washed with methanol, and dried in vacuo at 80° C. for 24 h. The yield was quantitative.

We claim:

1. An amorphous polymer of formula (I):

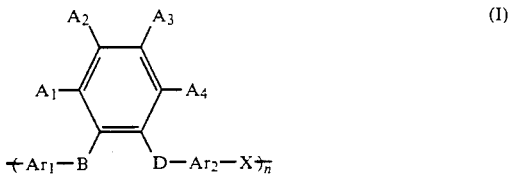

wherein $A_1$, $A_2$, $A_3$ and $A_4$ are each independently selected from hydrogen, aryl selected from the group consisting of phenyl, naphthyl and anthracyl, diphenylether or heteroaromatic radicals selected from the group consisting of pyridinyl, pyrazinyl, quinolinyl, thiophenyl, benzothiophenyl, furanyl and dibenzofuranyl, said aryl, diphenylether and heteroaromatic radicals being unsubstituted or substituted by a substituent selected from lower alkyl of 1 to 6 carbon atoms, lower alkoxy of 1 to 6 carbon atoms, lower thioalkyl of 1 to 6 carbon atoms, halogen, phenyl, naphthyl, anthracyl, diphenylether or heteroaromatic radicals selected from the group consisting of pyridinyl, pyrazinyl, quinolinyl, thiophenyl, benzothiophenyl, furanyl and dibenzofuranyl, B and D are both carbonyl groups CO, or B and D together represent a divalent radical of formula:

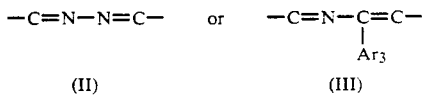

wherein $Ar_3$ is an aryl selected from the group consisting of phenyl, naphthyl and anthracyl, diphenylether or heteroaromatic radical selected from the group consisting of pyridinyl, pyrazinyl, quinolinyl, thiophenyl, benzothiophenyl, furanyl and dibenzofuranyl, unsubstituted or substituted by a substituent selected from lower alkyl of 1 to 6 carbon atoms, lower alkoxy of 1 to 6 carbon atoms, lower thioalkyl of 1 to 6 carbon atoms, halogen, phenyl, naphthyl, anthracyl, diphenylether or heteroaromatic radicals selected from the group consisting of pyridinyl, pyrazinyl, quinolinyl, thiophenyl, benzothiophenyl, furanyl and dibenzofuranyl, $Ar_1$ and $Ar_2$ are each phenylene radicals, unsubstituted or substituted 1 to 4 times by a substituent selected from lower alkyl of 1 to 6 carbon atoms, lower alkoxy of 1 to 6 carbon atoms, lower thioalkyl of 1 to 6 carbon atoms, halogen, phenyl, naphthyl, anthracyl, diphenylether or heteroaromatic radicals selected from the group consisting of pyridinyl, pyrazinyl, quinolinyl, thiophenyl, benzothiophenyl, furanyl and dibenzofuranyl, n is an integer of 20 to 200, X is a single bond, —O—R—O, —S— or —S—R—S—, wherein R is arylene selected from the group consisting of phenylene, naphthylene and anthracylene or aralkylidinylarylene of formula —Ph—$R_1$—Ph— in which $R_1$ is a straight chain or branched alkylene of 1 to 6 carbon atoms and Ph is phenylene, in which each arylene and phenylene moiety is unsubstituted or substituted by lower alkyl of 1 to 6 carbon atoms, lower alkoxy of 1 to 6 carbon atoms, lower thioalkyl of 1 to 6 carbon atoms, halogen, phenyl, naphthyl, anthracyl, diphenylether or heteroaromatic radicals selected from the group consisting of pyridinyl, pyrazinyl, quinolinyl, thiophenyl, benzothiophenyl, furanyl and dibenzofuranyl, and the alkylidine moiety of said aralkylidinylarylene is unsubstituted or fluoro-substituted alkylidine, said polymer having a glass transition temperature of at least 220° C., and provided that when B and D are both carbonyl groups CO, $A_1$ and $A_4$ are both selected from said aryl, diphenylether or heteroaromatic radicals.

2. A polymer of claim 1 in which B and D are both carbonyl groups.

3. A polymer of claim 1 in which B and D represent said divalent radical of formula (II) whereby B and D form part of a pyridazine ring.

4. A polymer of claim 1 in which B and D represent said divalent radical of formula (III), whereby B and D form part of a pyridine ring.

5. A polyketone of claim 2 wherein $A_2$ and $A_3$ are each independently selected from hydrogen and phenyl, $A_1$ and $A_4$ are both phenyl and X is selected from $OPhC(CH_3)_2PhO$, OPhO and OPhPhO in which Ph is phenylene.

6. A polyphthalazine of claim 3 wherein $A_1$, $A_2$, $A_3$ and $A_4$ are each independently selected from hydrogen and phenyl and X is —O—R—O in which R is selected from $OPhC(CH_3)_2$ PhO, and OPhPhO in which Ph is phenylene.

7. A polyisoquinoline of claim 4 wherein $A_1$, $A_2$, $A_3$ and $A_4$ are each independently selected from hydrogen and phenyl and X is —O—R—O in which R is selected from $OPhC(CH_3)_2$ PhO, OPhO and OPhPhO in which Ph is phenylene; and $Ar_3$ is phenyl.

8. A polyketone of claim 2 wherein $A_2$ and $A_3$ are each independently selected from hydrogen or phenyl and $A_1$ and $A_4$ are both phenyl.

9. A polyketone of claim 8 wherein $A_2$ and $A_3$ are both hydrogen.

10. A polyketone of claim 8 wherein $A_2$ and $A_3$ are both phenyl.

* * * * *